United States Patent
Hamilton (10) Patent No.: US 7,358,472 B2
(45) Date of Patent: *Apr. 15, 2008

(54) LOW POWER PHOTOTRANSISTOR-BASED WELDING HELMET PROVIDING REDUCED SENSITIVITY TO LOW INTENSITY LIGHT AND SHARP PHOTOTRANSISTOR RESPONSE TO HIGH INTENSITY LIGHT

(75) Inventor: Thomas Joe Hamilton, Holland, MI (US)

(73) Assignee: Jackson Products, Inc., Chesterfield, MO (US)

( * ) Notice: Subject to any disclaimer, the term of this patent is extended or adjusted under 35 U.S.C. 154(b) by 381 days.

This patent is subject to a terminal disclaimer.

(21) Appl. No.: 11/363,391

(22) Filed: Feb. 27, 2006

(65) Prior Publication Data

US 2006/0138302 A1    Jun. 29, 2006

Related U.S. Application Data (60) Continuation of application No. 11/054,927, filed on Feb. 10, 2005, now Pat. No. 7,005,624, which is a continuation of application No. 10/827,014, filed on Apr. 19, 2004, now Pat. No. 6,855,922, which is a division of application No. 09/659,100, filed on Sep. 11, 2000, now Pat. No. 6,815,652.

(51) Int. Cl.
*G01J 1/32* (2006.01)

(52) U.S. Cl. .................. 250/205; 250/214 R (58) Field of Classification Search ............... 250/205, 250/214 R
See application file for complete search history.

(56) References Cited

U.S. PATENT DOCUMENTS

| | | | |
|---|---|---|---|
| 4,240,709 A | 12/1980 | Hornell | |
| 5,248,880 A | 9/1993 | Fergason | |
| 5,751,258 A | 5/1998 | Fergason et al. | |
| 6,070,264 A | 6/2000 | Hamilton | |
| 6,483,090 B1 | 11/2002 | Bae | |
| 6,614,409 B1 | 9/2003 | Bae | |
| 6,941,577 B2 * | 9/2005 | Ackermann | 2/8.8 |

FOREIGN PATENT DOCUMENTS

| | | |
|---|---|---|
| EP | 01121569 | 3/2003 |
| GB | 1430183 | 3/1976 |
| WO | WO 94/25892 | 11/1994 |

OTHER PUBLICATIONS

Data Sheet; Vishay; "Silicon NPN Phototransistor"; Document No. 81556; May 20, 1999; 5 pages.

* cited by examiner

*Primary Examiner*—Que T Le
(74) *Attorney, Agent, or Firm*—Dunlap Codding & Rogers (57) ABSTRACT

An auto darkening eye protection device including a shutter assembly, a light sensing circuit, a control circuit and a power source. The shutter assembly is adjustable to a plurality of shade levels. The phototransistor of the light sensing circuit senses light from a welding arc and provides an output of the light sensing circuit indicative of the shade level at which the shutter assembly should be operated. The phototransistor is configured for surface mount and has an external base connection connected to the base of the phototransistor. The control circuit is configured to receive the output from the light sensing circuit and provide a drive signal to the shutter assembly responsive to said output, drives the shutter assembly to one of said plurality of shade levels. The present invention provides reduced power consumption, improved attenuation of low intensity light signals, a sharp rise time from the phototransistor in response to high intensity light, and allows implementation into a smaller sleeker eye protection device.

19 Claims, 7 Drawing Sheets

LOW POWER PHOTOTRANSISTOR-BASED WELDING HELMET PROVIDING REDUCED SENSITIVITY TO LOW INTENSITY LIGHT AND SHARP PHOTOTRANSISTOR RESPONSE TO HIGH INTENSITY LIGHT

CROSS-REFERENCE TO RELATED APPLICATIONS

The present patent application is a continuation of U.S. Ser. No. 11/054,927, (U.S. Pat. No. 7,005,624), filed on Feb. 10, 2005, which is continuation of U.S. Ser. No. 10/827,014, (U.S. Pat. No. 6,855,922), filed on Apr. 19, 2004, which is a divisional patent application of U.S. Ser. No. 09/659,100, (U.S. Pat. No. 6,815,652) filed on Sep. 11, 2000, the entire content of both applications are hereby expressly incorporated by reference.

BACKGROUND OF THE INVENTION

The present invention relates to the field of auto-darkening eye protection devices, such as welding helmets having a shutter (or lens) assembly that automatically darkens upon the detection of a welding arc. A photosensitive device such as a photodiode or a phototransistor may be used to sense the intensity of light incident on the area of the shutter assembly so as to provide an indication to the circuitry controlling the shutter assembly that the shutter assembly needs to be driven to either a dark state or a clear state. If a welding arc is present, the welding helmet protects the eyes of the welder from any danger caused by the intensity of the welding arc by driving the shutter assembly to a dark state, thereby decreasing the amount of energy passing through the lens to the welder's eyes. U.S. Pat. Nos. 4,385,806, 4,436,376, 4,540,243, Re. 32,521, 5,248,880, 5,252,817, 5,347,383, 5,533,206, 5,751,258, 5,959,705, 6,067,129, and 6,070,264 each disclose various shutter assemblies and liquid crystal driver electronics that can be used in conjunction with the present invention. The disclosures of these above-mentioned patents are hereby incorporated in their entireties by reference.

Commonly-owned U.S. Pat. No. 5,347,383 discloses a driving circuit for a liquid crystal shutter. The sensor circuitry of this invention utilizes a photodiode to detect the occurrence of welding. This sensor circuitry also utilizes a comparator to compare the sensed light signal with a threshold value to determine whether the shutter assembly should be driven to a dark or clear state. Additionally, the '383 patent discloses the use of a 9 V supply.

While the invention disclosed in this patent functioned for its intended purpose, a need was felt for an improvement in the power consumption by the sensor circuit. As incident light increases on a photodiode, the voltage across the photodiode will begin to saturate. To prevent the photodiode from saturating, a steadily increasing load must be put on the photodiode which leads to excessive power consumption.

To alleviate the excessive power consumption inherent in a photodiode-based sensor circuit, a phototransistor has been utilized as a weld sensor. The use of a phototransistor allows the use of feedback to bias the phototransistor so that less current is needed to keep the phototransistor in its operational mode. Commonly-owned U.S. Pat. Nos. 5,252,817, 5,248,880, 5,751,258, and 6,070,264 are illustrative of sensor circuits using phototransistors as weld sensors. Each of these patents discloses a sensor circuit wherein the output of the phototransistor is fed into a comparator. The comparator compares the phototransistor output with a threshold level. If the phototransistor output exceeds the threshold level, the drive circuitry is activated to darken the shutter assembly. If the phototransistor output does not exceed the threshold level, the drive circuitry operates the shutter assembly in a clear state. While the circuits disclosed in these patents utilize feedback to bias the phototransistor and avoid the excessive drawing of current, heavy loads were still needed. The circuits implementing such designs used voltage supplies ranging from 5.6 V to 9 V. Therefore, a need was still felt for a sensor circuit having improved power consumption characteristics.

Moreover, the phototransistors used in the prior art designs were metal can phototransistors. Metal can phototransistors are relatively big and bulky. Their size, height and relative difficulty in mounting serves as a limiting factor in the ability of designers to reduce the size of the units in which the sensor circuit is implemented. Thus, a need was felt to use a smaller and more compact phototransistor that is more easily mountable to a circuit board to produce a smaller, sleeker unit while still having the ability to maintain a constant signal level without excessive loading or the drawing of excessive current.

Additionally, the sensor circuits of the prior art produced an output voltage from the phototransistor in response to incident light intensity as seen in FIG. 3 of the '880 and '817 patents. As can be seen, low light intensities produce a steep rise in output of the phototransistor. Because of the power drain caused by the response of the phototransistor to low intensity incident light, it is desirable that the phototransistor be configured to minimize the phototransistor output signal when the sensor circuit is exposed to low intensity incident light. Thus, a need existed for a sensor circuit that provided greater attenuation in the response of the phototransistor to low intensity incident light.

While it is desirable to minimize the phototransistor output when the sensor circuit is exposed to low intensity incident light, the phototransistor still must be able to quickly increase its output in response to a transition from low intensity light to high intensity light, such as the light provided by a welding arc. Thus, an ever present need exists within the art to sharpen the rise provided by the phototransistor in response to sharp increases in light intensity.

Also, the sensor circuitry of the prior art used a comparator to correlate the sensed light signal with the desired shade level. The comparator compared the output of the phototransistor with a threshold voltage signal to determine whether the shutter assembly should be driven to a dark state or a clear state. This design required additional circuitry to set the threshold voltage level. This additional circuitry not only complicated circuit design, but also increased the drain on the power supply. Thus, a need was felt to simplify the sensor circuitry to provide a more power-efficient way of correlating the phototransistor output to the proper shade setting of the shutter assembly.

BRIEF SUMMARY OF THE INVENTION

In order to solve these and other problems in the prior art, the inventor herein has succeeded in designing and developing an improved welding detection circuit utilizing a novel phototransistor-based sensor circuit. This sensor circuit comprises a phototransistor biased via a feedback circuit and having an output connected to an amplifier. The sensor circuit can be connected to a power supply and a control circuit to drive a shutter assembly to either a dark state or a clear state depending upon the intensity of incident light.

One feature of the present invention is the use of a resistor coupled between the base and emitter of the phototransistor. This resistor helps reduce the current produced by the sensor during low ambient light conditions, thereby attenuating the phototransistor output in response to low intensity light signals, and helps produce a sharply rising voltage from the phototransistor in response to high intensity light signals. Preferably, the feedback circuit also includes a second resistor coupled between the emitter of a feedback transistor and ground to further attenuate phototransistor output in the presence of low intensity ambient light.

Another feature of the present invention is its use of a planar phototransistor. Because of the planar phototransistor's small size, as compared to the metal can phototransistors used in the prior art, and because of the planar transistor's ability to maintain a constant signal level without excessive loading or the drawing of excessive current, the use of a planar phototransistor not only performs as well as metal can phototransistors, but also allows a reduction in the size of the unit in which the circuit is implemented. Preferably, the planar phototransistor is configured for a surface mount to further simplify construction of the circuit.

Another feature of the present invention is its use of a closed loop noninverting amplifier to provide a gain for the phototransistor output. The gain of the amplifier is preferably set so that a sufficient output voltage will be generated to activate the shutter assembly when the phototransistor produces an output indicative of the presence of a welding arc. Preferably, a capacitor is coupled between the phototransistor output and noninverting input of the amplifier to block the DC portion of the phototransistor output.

Another feature of the present invention is its use of the energy saved by an improved and efficient circuit design to recharge a rechargeable battery. By recharging the battery, the present invention extends the battery life of the invention's power supply.

Figure 5:
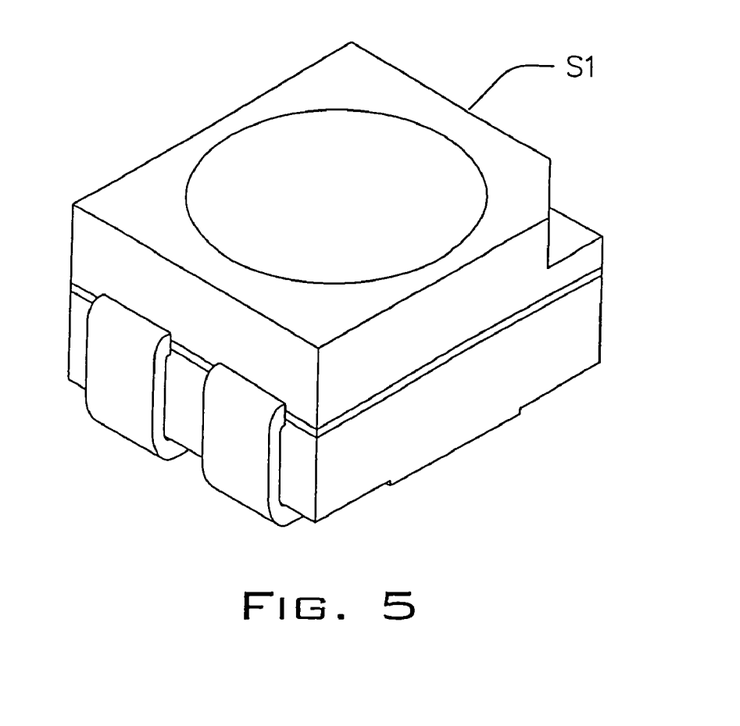
FIG. 5 is a perspective view of a surface mount phototransistor utilized in the present invention.

Another feature of the present invention is its use of a solar cell to reduce the circuit's power consumption. By using a solar cell to power various components of the circuit, the present invention prevent those components from acting as a drain on the power supply when the invention is left unexposed to light. FIG. 5 is a perspective view of a surface mount phototransistor utilized in the present invention. Often, while not in use, a welding helmet will be left in a dark room or left face down on a table. When in these conditions, it is undesirable for the circuit to operate as a drain on the power supply. When, the welding helmet is in use, it will be either outdoors, in a lighted room, or in a dark environment with the presence of welding arc. In such conditions, it is desirable to use the light incident on the welding helmet to power the circuitry therewithin.

The present invention uses the solar cell to power the phototransistor and the amplifier that is coupled to the output of the phototransistor, thus preventing those two components from draining the power supply when the welding helmet is left unexposed to light.

The present invention also uses the solar cell to power an activation circuit, the activation circuit functioning to activate a signal generator. The signal generator, once activated, generates the voltage level and frequency signal to be used to drive the shutter assembly to a dark state. The generation of this signal acts as a drain on the power supply. By using the solar cell to power the activation circuit, the present invention improves the circuit's power consumption by triggering the signal generator when light is incident on the welding helmet.

Yet another feature of the present invention is its use of a selector circuit for selecting the drive signal that will be delivered to the shutter assembly. If the sensor circuit indicates to the selector circuit that a welding arc is present, the selector circuit will cause a dark state drive signal to be delivered to the shutter assembly. If the sensor circuit indicates to the selector circuit that no welding arc is present, the selector circuit will cause a "clear state" drive signal to be delivered to the shutter assembly. The selector circuit uses a transistor as a switch to control the selection of the drive signal. An RC circuit is part of the selector circuit. The RC circuit utilizes its RC time constant to delay the transition of the "dark state" drive signal to the "clear state" drive signal, thus preventing the shutter assembly from switching to a clear state during brief "off" periods in the weld pulsations that exist with various weld types.

While the principal advantages and features employed are explained above, a fuller understanding of the invention may be attained by referring to the drawings and description of the preferred embodiment which follows.

DETAILED DESCRIPTION OF THE PREFERRED EMBODIMENT

Figure 1:
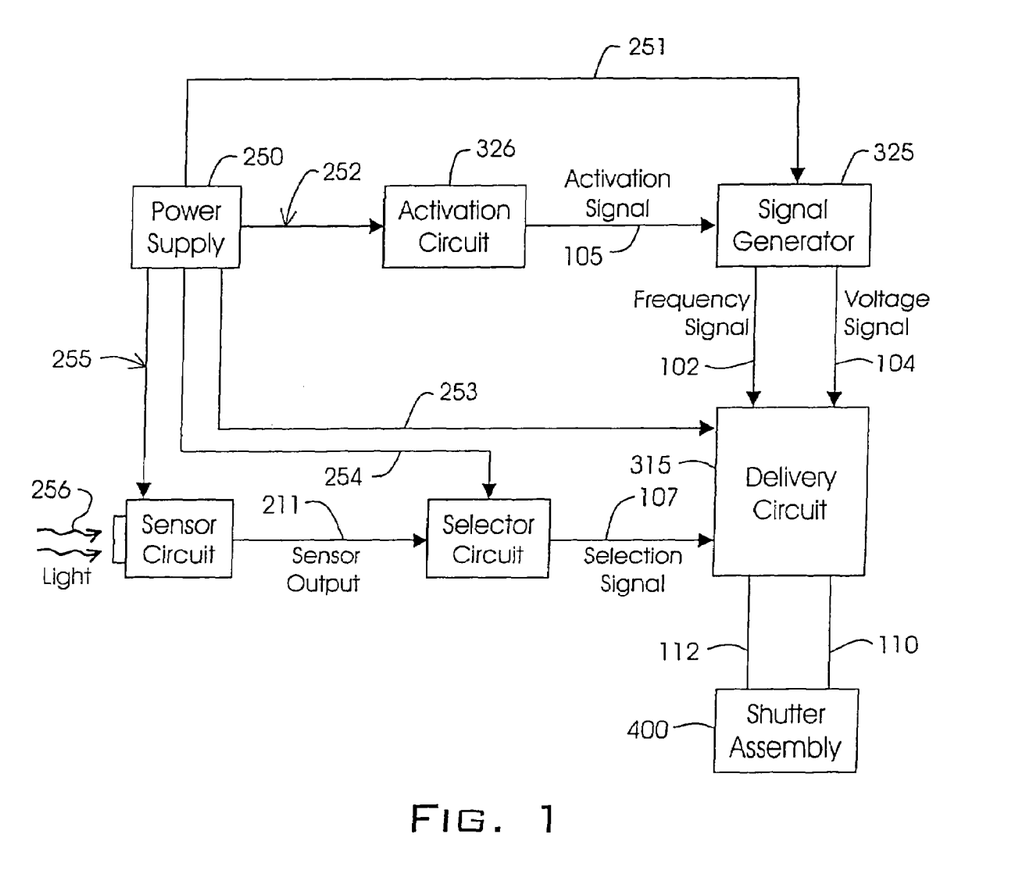
FIG. 1 is a block diagram of the circuit of the present invention.

A block diagram of the circuit of the present invention is depicted in FIG. 1. As can be seen, a power supply 250 is connected via power lines 251, 252, 253, 254, and 255 to the sensor circuit 200, activation circuit 326, selector circuit 316, signal generator 325, and delivery circuit 315. The power supply 250 furnishes the circuit with the power necessary for operation. Activation circuit 326, selector circuit 316, signal generator 325, and delivery circuit 315 function together to control the shutter assembly 400 depending upon the signals received from power supply 250 and sensor circuit 200.

Activation circuit 326 receives power from the power supply 250 and sends an activation signal to the signal generator 325. Upon activation by the activation circuit, the signal generator 325 generates a frequency signal 102 and a voltage signal 104 and sends the two signals 102 and 104 to the delivery circuit 315. The delivery circuit 315 uses the frequency signal 102 and the voltage signal 104 to assemble a "dark state" drive signal for the shutter assembly 400.

The sensor circuit 200 senses incident light 256 and produces an output signal representative of the amount of incident light sensed. This output signal 211 is sent to selector circuit 316. Depending upon the sensor circuit output, the selector circuit delivers a selection signal 107 to the delivery circuit 315. If the sensor circuit 200 produces an output representative of the presence of high intensity light, such as the light produced by a welding arc, the selector circuit will send a selection signal 107 to the delivery circuit indicating that a "dark state" drive signal should be delivered to the shutter assembly 400. If the sensor circuit 200 produces an output representative of the presence of low intensity light (i.e., no welding arc is present), the selector circuit will send a selection signal 107 to the delivery circuit indicating that a "clear state" drive signal should be delivered to the shutter assembly 400. The delivery circuit 315 uses the selection signal 107 to determine the voltage level for the drive signals. If the selection signal 315 indicates that a "dark state" drive signal is needed, the delivery circuit will assemble a drive signal having a frequency set by the frequency signal 102 and voltage levels transitioning between the voltage signal 104 and the voltage of the power signal 253. If the selection signal 315 indicates that a "clear state" drive signal is needed, the delivery circuit will assemble a drive signal having a constant voltage level set by the voltage of the power signal 253. The delivery circuit 315 delivers this drive signal to the shutter assembly 400 via drive signal lines 110 and 112. If the drive signal is a "dark state" drive signal, the shutter assembly 400 will be driven to a dark state. If the drive signal is a "clear state" drive signal, the shutter assembly 400 will be driven to a clear state.

Figure 2:
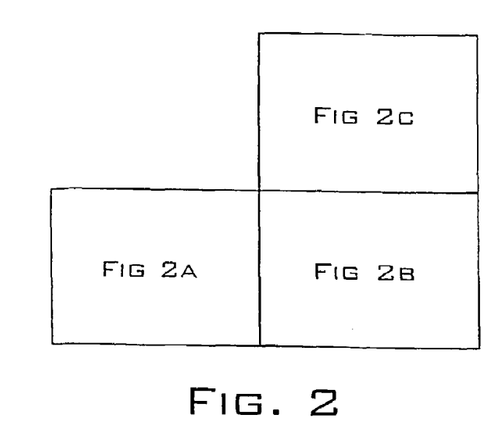
FIG. 2 is a schematic diagram of the circuit of the present invention.
Figure 2A:
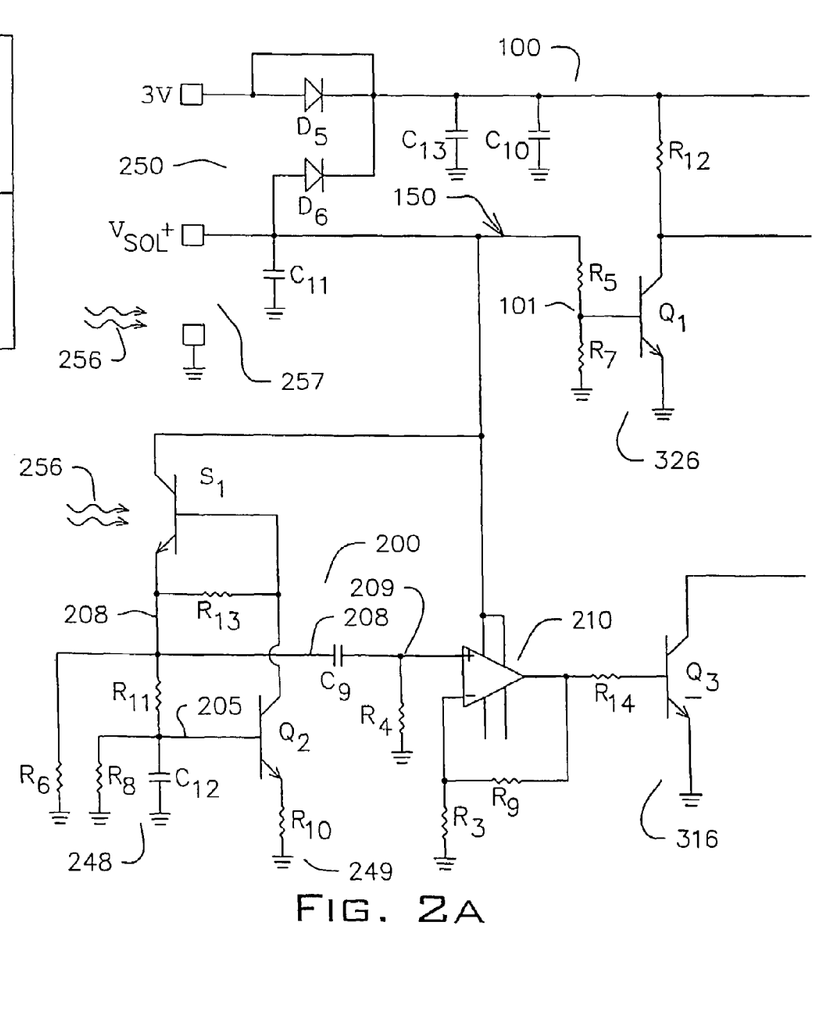
Figure 2B:
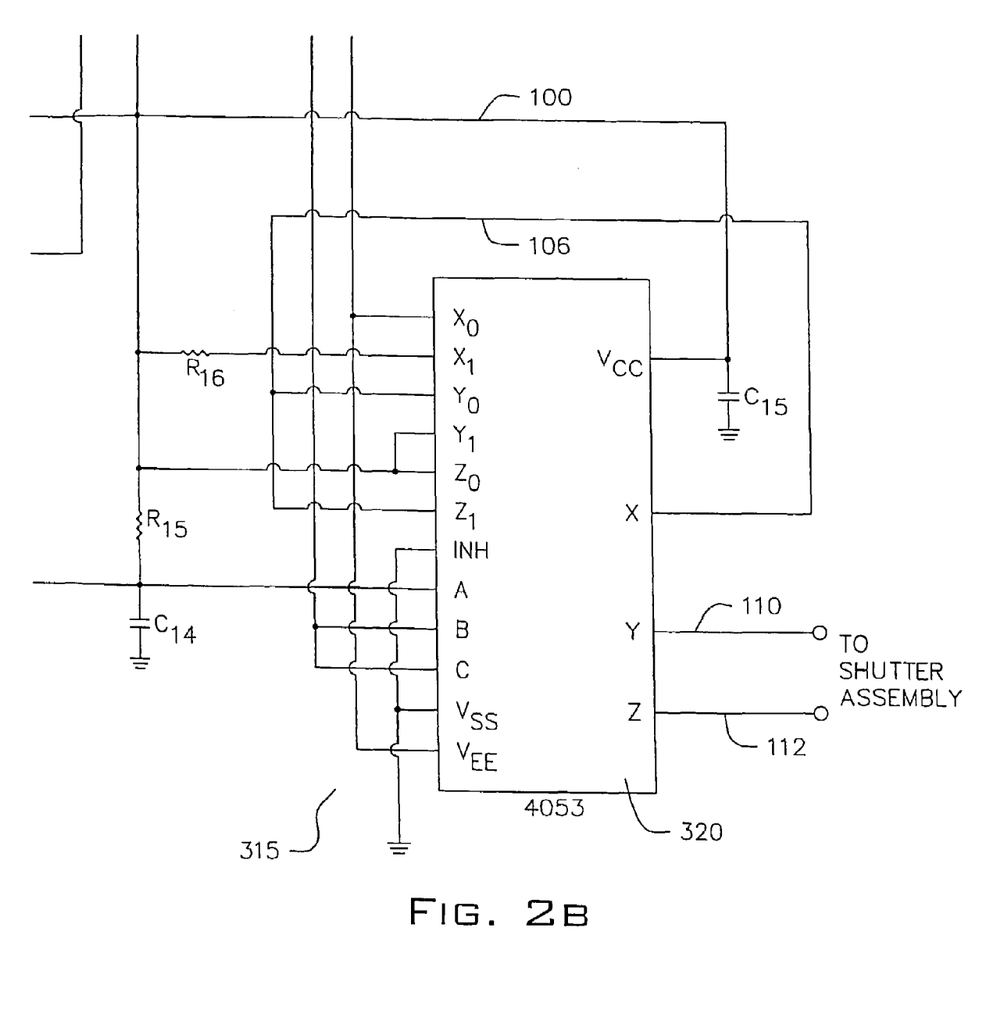
Figure 2C:
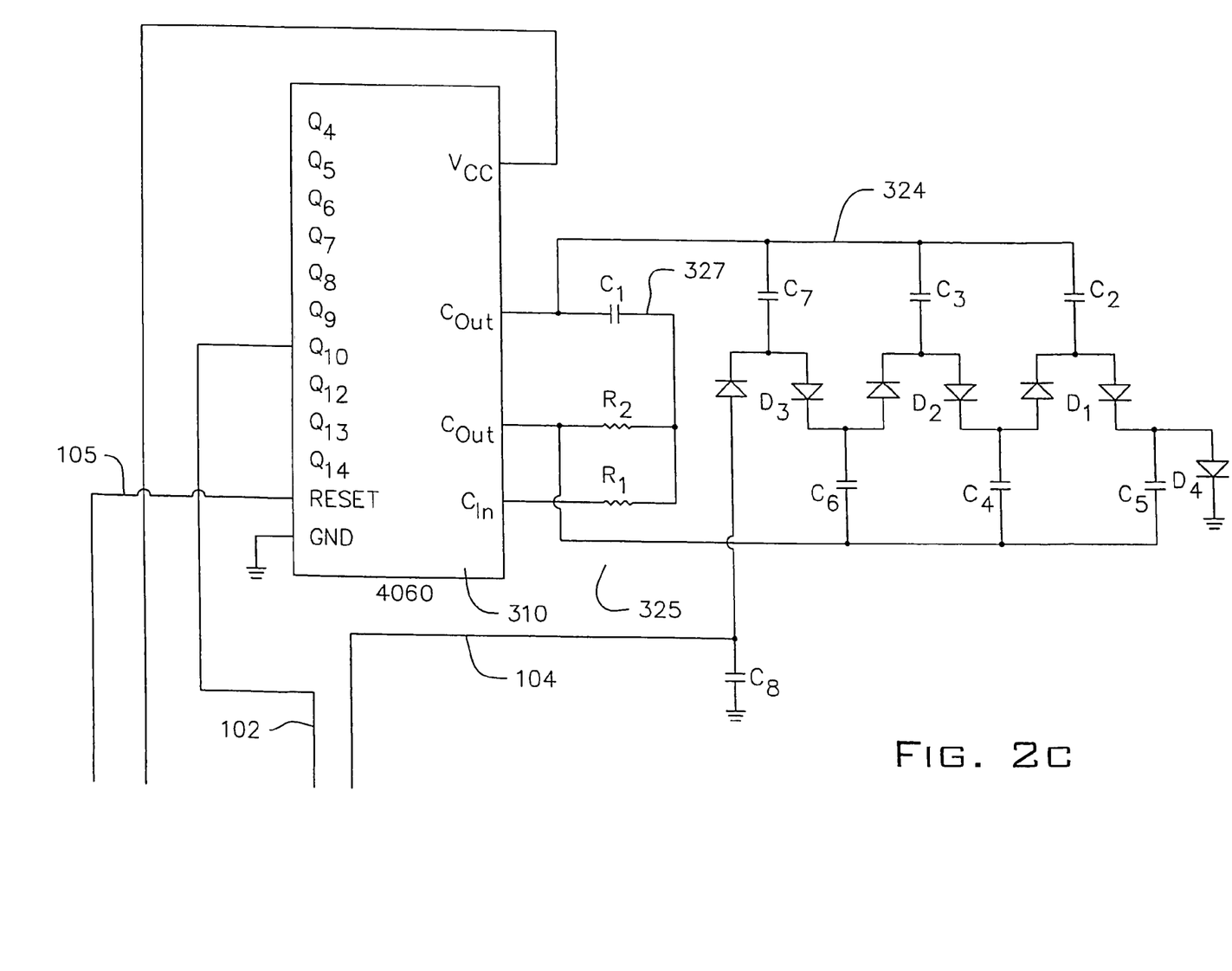

Referring to FIG. 2, a detailed schematic of the circuit depicted in the block diagram of FIG. 1 is shown. Preferably, power supply 250 includes a rechargeable 3 V supply and a solar cell 257. However, a single power source, either a battery or a solar cell, can be used without dramatically altering the operation of the circuit. It is also preferable that the solar cell serve as the circuit's primary power source, with the 3 V supply functioning to provide additional power to various circuit components when the solar cell voltage falls below the battery voltage. The solar cell power supply supplemented by the 3 V rechargeable supply is seen on line 100 (the signal on this line will be referred to as the 3 V signal). The solar cell power supply that is not supplemented by the 3 V rechargeable supply is seen on line 150. Because of the improved power efficiency of the present invention, the circuit can utilize unused energy to recharge the 3 V supply.

To implement these preferences, the 3 V supply is coupled to diode D5 as shown, with the output of D5 fed back to its input. Also, diode D6 is coupled between the output of D5 and $V_{SOL+}$ as shown. Capacitor C11 is coupled between $V_{SOL+}$ and ground as shown. C11, preferably 0.1 μF, serves as a filter for $V_{SOL+}$. Capacitors C10 and C13, coupled between the 3 V supply and ground, function to filter and smoothen the 3 V supply on line 100. Preferably, C10 and C13 are each 3.3 μF. When light 256 reaches the solar cell, the voltage $V_{SOL+}$ will increase until the solar cell reaches approximately 3.3 V (depending on the amount of incident light). The solar cell also functions to recharge the 3 V supply.

The power supply 250 delivers a 3 V signal along line 100 to the $V_{CC}$ pin of the 4060 chip 310, to the $V_{CC}$ pin of the 4053 chip 320, to the X1 pin of the 320 (through R16), to the Y1 pin of 320, to the Z0 pin of 320 and to the collector of transistor Q3 (through resistor R15). The power supply delivers $V_{SOL+}$ along line 150 to the collector of the phototransistor S1, to the supply for amplifier 210, and to the base of transistor Q1 (through resistor R5).

When light incident on the solar cell increases, thereby causing an increase in voltage on line 150, the voltage at the base of control transistor Q1 will increase. Once the voltage at the base of Q1 reaches approximately 0.6 V, Q1 will turn "on" to activate the signal generator 325. By only activating the signal generator when there is light incident on the solar cell, the power drain on the circuit is reduced because the signal generator will only be active when the welding helmet is likely to be in use. When the welding helmet is not in use, it is typically left in either a dark room or with its solar cell face down, which in either case would prevent the solar cell from triggering Q1. With Q1 "off," the signal generator will not drain the power supply. When the welding helmet is in use, it will be exposed to outdoor light, indoor light, or weld light. In these situations, the solar cell will trigger Q1 to activate the signal generator.

The voltage at the base of Q1 is set by the resistor divider circuit formed by the junction 101 of R5 and R7 as shown. Preferably, R5 is 2MΩ and R7 is 1MΩ. The emitter of Q1 is grounded. The collector of Q1 is connected to the 3 V supply through R12. The collector of Q1 is also connected to the RESET pin of 310 via line 105. The signal on line 105 serves to activate the signal generator 325. Once Q1 is turned "on," the voltage at the collector of Q1 will change from 3 V to substantially 0 V as a path to ground is created. This transition causes the signal on line 105 to go from high to low, which removes the reset signal from 310. With the reset signal low, 310 begins toggling $C_{IN}$ and $C_{OUT}$. The two $C_{OUT}$ pins and the $C_{IN}$ pin of 310 are connected to a charge pump 324 as shown. Charge pump 324 comprises capacitors C2, C3, C4, C5, C6, and C7 and diodes D1, D2, D3, and D4 as shown. The charge pump 324 functions to generate the signal used to set the voltage level of the "dark state" drive signal. This voltage level is sent to the delivery circuit 315 via line 104. Preferably, this voltage level is set to be approximately −15 V using charge pump capacitors C2 through C7 of 0.1 μF apiece. The −15 V signal on line 104 is stored in capacitor C8, which is preferably 6.8 μF. RC circuit 327 sets the frequency of the charge pump. Preferably, the RC circuit is designed to produce a frequency of approximately 550 Hz using an R1 of 2 MΩ, an R2 of 1 MΩ, and a C1 of 680 pF. This frequency can be passed through a binary counter in chip 310 to divide the frequency to about 0.5 Hz. The 0.5 Hz signal exits 310 through line 102 at pin Q10 as shown. Line 102 delivers this frequency signal to pins B and C of the 4053 chip 320. This frequency serves as the frequency for the "dark state" drive signal.

The output of the sensor circuit on line 211 is coupled to the base of control transistor Q3. The collector of Q3 is connected to a 3 V power supply through R15. The collector of Q13 is also coupled to the ground through capacitor C14. The collector of Q3 is also coupled to pin A of the 4053 chip 320 via line 107.

Pins B and C of the chip 320 receive the frequency signal 102 from signal generator 325. Thus, pins B and C toggle at the frequency of frequency signal 102, which is preferably 0.5 Hz. Pin A controls the selection of pins X0 and X1. When pin A is "high," pin X1 is selected. When pin A is "low," pin X0 is selected. Pin B controls the selection of pins Y0 and Y1. When pin B is "high," pin Y1 is selected. When pin B is "low," pin Y0 is selected. Pin C controls the selection of pins Z0 and Z1. When pin C is "high," pin Z1 is selected. When pin C is "low," pin Z0 is selected. The selection of a particular pin means that the signal on the selected pin will be passed on to the output associated with the pair. For example, when pin A is "high," pin X1 is selected and the signal at pin X1 is passed through to output pin X. When pin B is "low," pin Y0 is selected and the signal at pin Y0 is passed through to output pin Y.

Pin X0 is connected to the B15 V voltage signal supplied on line 104 by signal generator 325. Pin X1 is connected to the 3 V power supply via R16. Thus, the status of the signal at pin A determines whether a B15 V signal or a 3 V signal is passed through to output pin X. Pin Y0 is connected to output pin X via line 106. Thus, whatever signal is passed to X will be received at Y0. Pin Y1 is connected to the 3 V supply. Pin Z0 is also connected to the 3 V supply. Pin Z1, like pin Y0, is connected to output pin X via line 106. Output pins Y and Z are connected to the shutter assembly 400.

The signal on line 211 at the output of the sensor circuit 200 controls whether Q3 is turned "off" or "on." Q3 needs a signal on line 211 of about 0.6 V to turn "on." The sensor circuit 200 is configured to produce an output of at least 0.6 V when a welding arc is present. If no welding arc is present, Q3 will not receive a sufficient voltage on line 211 to turn "on."

When in the "off" state, the voltage on line 107 will be "high," that is, substantially equal to the 3V supply. While pin A is "high," the signal at pin X1 is passed through to output pin X. Since pin X1 is substantially 3 V, this signal will be passed to input pins Y0 and Z1. Thus, when pin A is "high" (which corresponds to no welding arc being present), pins Y0, Y1, Z0, and Z1 will all receive a substantially 3 V signal. Thus, as pins B and C alternate from "high" to "low" at 0.5 Hz (the frequency of signal 102) and pins Y0 and Z0, and pins Y1 and Z1 are alternately passed through to output pins Y and Z, the resultant signal on lines 110 and 112 will be a substantially steady 3 V signal. This steady 3 V signal on lines 110 and 112 corresponds to a "clear state" drive signal, that is, the drive signal which will transition the shutter assembly to a clear state.

When the output of the sensor circuit 200 is sufficient to turn "on" Q3 (indicating the presence of a welding arc), the signal on line 107 will quickly go from 3 V to 0 V as a path to ground is created through Q3. Thus, pin A will go "low." When pin A is "low," the signal at pin X0 is passed through to output pin X. Since pin X0 is B15 V, this B15 V signal will be received at pins Y0 and Z1. As pins B and C alternate from "high" to "low" at 0.5 Hz (the frequency of signal 102), the value of Y will be 3 V when the value of Z is B15 V and vice versa. The signal on line 110 will alternate between 3 V and B15 V at 0.5 Hz. The signal on line 112 will alternate between 3 V and B15 V at 0.5 Hz out of phase with the signal on line 110. Thus, the resultant signal delivered to the shutter assembly 400 will be an 18 V square wave having a 0.5 Hz frequency. This 18 V, 0.5 Hz, square wave corresponds to a "dark state" drive signal, that is, the drive signal which will transition the shutter assembly to a dark state.

When the welding arc ceases, the voltage on line 211 will be insufficient to maintain Q3 in an "on" state. Once Q3 turns "off," the signal on line 107 will return to a "high" state. However, this transition will not be instantaneous due to the RC circuit formed by R15 and C14. The transition of 107 from "low" to "high" will be delayed as C14 charges. By selecting the RC time constant for R15 and C14, the delay can be set to accommodate brief "off" periods in the "on/off" pulsating light of various welding conditions. Before C14 recharges, the light pulse of the weld arc will pass through the sensor circuit 200 and reactivate Q3 to cause a quick transition on line 107 back to "low." Preferably R15 is 2 MΩ and C14 is 0.1 µF. The "low-to-high" transition on line 107 will be about 0.25 seconds in a circuit with those parameters.

Sensor circuit 200 includes a phototransistor S1 coupled to a feedback circuit 249. Additionally, resistor R13 is coupled between the base and emitter of the phototransistor. The output of phototransistor S1 is sent to line 208. A load resistor R6 is connected between line 208 and ground. Additionally, a capacitor C9 couples line 208 to line 209. Resistor R4 is connected between line 209 and ground. Line 209 is also connected to the noninverting input of amplifier 210. Amplifier 210 is preferably configured as closed loop noninverting amplifier wherein the R9 and R3 feedback loop is connected to the inverting input of amplifier 210 as shown. The output of amplifier 210 on line 211 serves as the sensor circuit output. Line 211 is connected to the input of selector circuit 316.

The solar cell 257 powers phototransistor S1 and amplifier 210 via line 150. Thus, if the solar cell is left unexposed to incident light, phototransistor S1 and amplifier 210 will not receive power, thus preventing the phototransistor and amplifier from draining the power supply when the welding helmet is not in use (when not in use, the welding helmet is typically not exposed to light).

The feedback circuit 249 for the phototransistor S1 comprises a resistor capacitor circuit 248 connected between the emitter of the phototransistor and ground, and a feedback transistor Q2 having a base coupled to line 205 of the resistor capacitor circuit 248, a collector coupled to the base of the phototransistor, and an emitter coupled to the ground via resistor R10.

Phototransistor S1 serves as the weld sensor. It receives an input of incident light 256 and produces an output on line 208 representative of the intensity of the incident light. The phototransistor S1 used in the present invention is preferably a planar phototransistor configured for a surface mount. The planar phototransistor is smaller than conventional metal can phototransistors, thus allowing a reduction in size of the unit in which the sensor circuit is implemented. While the metal can phototransistors used in the sensor circuits of the prior art had a thickness of about ½ inch, the planar phototransistors with a surface mount used in the present invention have a thickness of only about ¼ inch. This reduction is thickness allows the sensor circuit to be implemented into a smaller and sleeker unit. Further, the surface mount configuration of the phototransistor S1 allows the phototransistor to be easily affixed to a circuit board. The inventor herein has found that the TEMT4700 silicon npn phototransistor manufactured by Vishay-Telefunken is an excellent phototransistor for the present invention as it has a smaller size than conventional metal can phototransistors and allows the sensor circuit to maintain a constant signal level without excessive loading or the drawing of excessive current.

The resistor capacitor circuit 248 and the feedback transistor Q2 in the phototransistor feedback circuit 249 function to adjust the sensitivity of the phototransistor S1. The resistors R8 and R11 and capacitor C12 are chosen to be of a size to provide a relatively large time constant, and therefore a relatively slow response to changes in voltage on line 208. The delay exists because of the time it takes for the voltage on line 205 to charge to an amount sufficiently large to activate Q2. Exemplary values for R8 and R11 are 1 MΩ and 2 MΩ respectively. An exemplary value for C12 is 0.1 µF. A detailed description of the operation of the resistor capacitor circuit 248 and feedback transistor Q2 can be found in prior U.S. Pat. Nos. 5,248,880 and 5,252,817, the disclosures of which have been incorporated by reference.

R13 functions to attenuate phototransistor output in response to low intensity incident light by essentially shutting down the phototransistor when low intensity light is present. R13 further aids the response of the phototransistor by enabling the phototransistor to sharply increase its output when high intensity light is detected. R10, connected between the emitter of Q2 and ground further improves the sensor circuit by attenuating phototransistor output in response to low intensity light signals. Load resistor R6 is coupled between phototransistor output 208 and ground helps to further attenuate phototransistor output when low intensity light is incident upon the phototransistor. An exemplary value for R10 is 20 kΩ. An exemplary value for R6 is 1 MΩ.

Figure 3A:
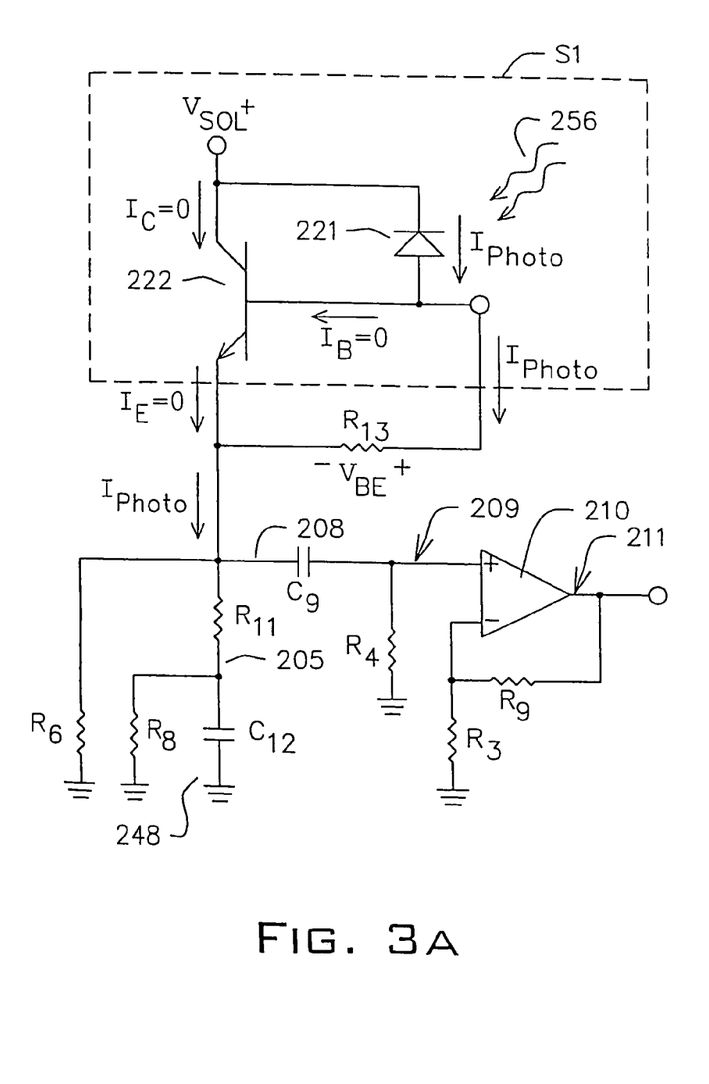
FIG. 3a is a schematic diagram of an equivalent circuit for the sensor circuit when both the phototransistor and feedback transistor are "off."
Figure 3B:
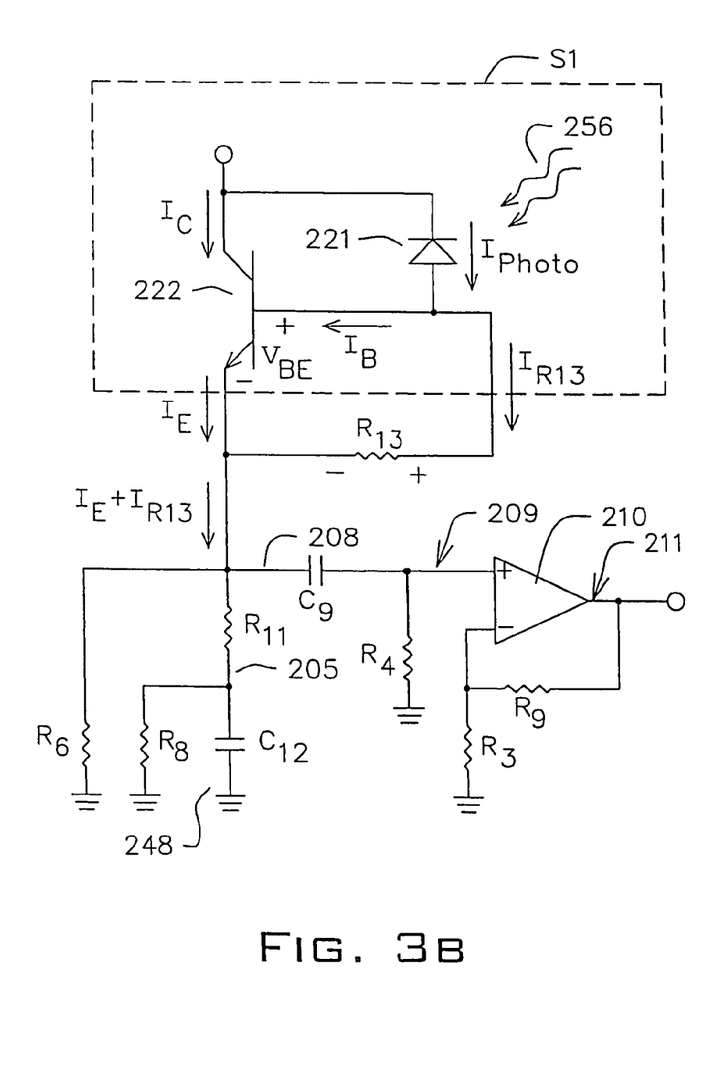
FIG. 3b is a schematic diagram of an equivalent circuit for the sensor circuit when the phototransistor is "on" and the feedback transistor is "off."
Figure 3C:
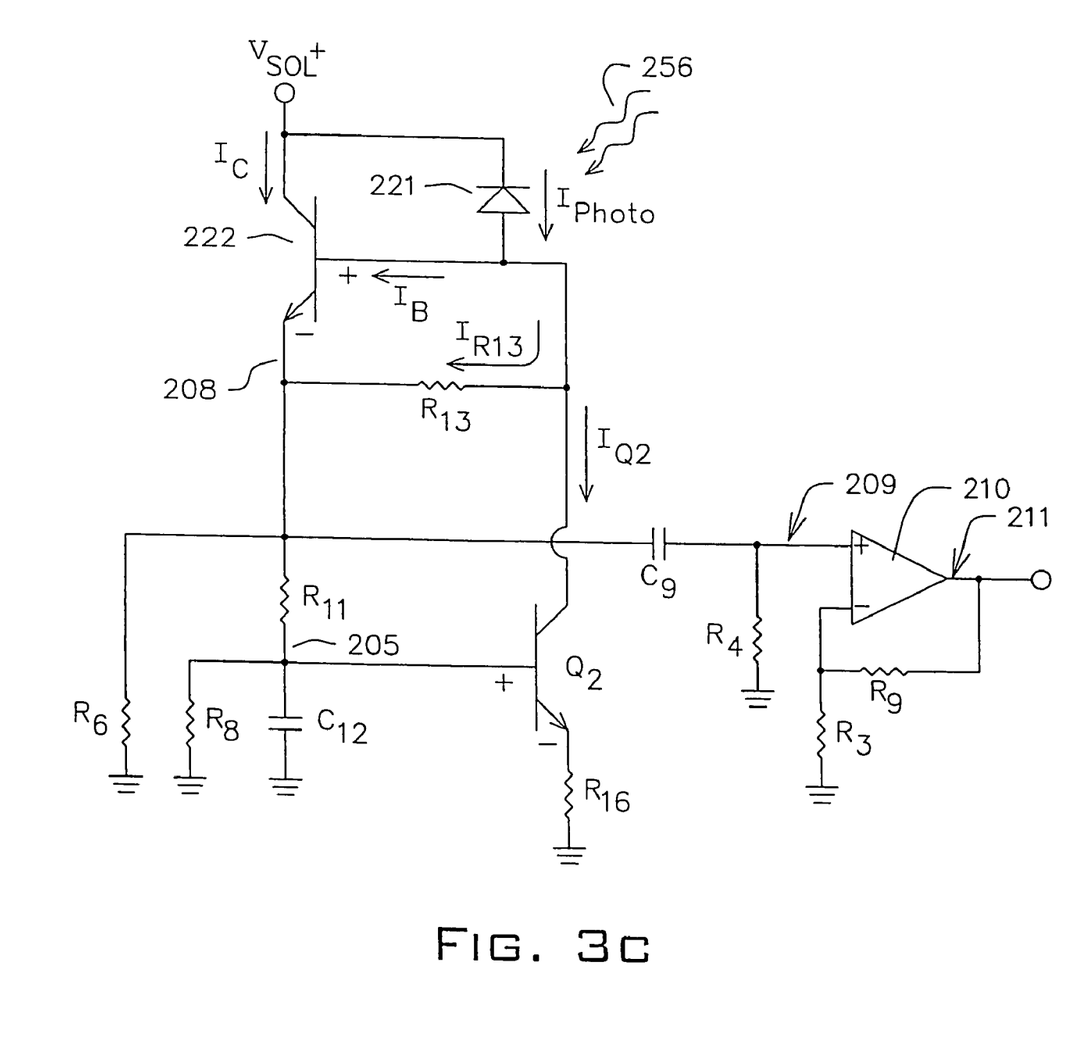
FIG. 3c is a schematic diagram of an equivalent circuit for the sensor circuit when both the phototransistor and the feedback transistor are "on."

Referring to FIGS. 3a, 3b, and 3c, the operation of the sensor circuit 200 will be described. First, the phototransistor has operational characteristics similar to a photodiode whose output is fed into the base of a conventional npn transistor. The equivalent circuit for a phototransistor is depicted in FIGS. 3a, 3b, and 3c. Photodiode 221 is connected between the base and collector of npn transistor 222. Incident light will produce a photocurrent, $I_{PHOTO}$, from the photodiode 221. $I_{PHOTO}$ serves to feed the base of the transistor 222. However, in the sensor circuit of the present invention, resistor R13 is also coupled between the base and emitter of the phototransistor. Thus, in the equivalent circuit model, R13 is connected between the base and emitter of transistor 222 as shown.

When light 256 first reaches the phototransistor, the phototransistor S1 is in the "off" state. Additionally, feedback transistor Q2 is in the "off" state. FIG. 3a depicts the equivalent circuit model for the sensor circuit 200 in this mode of operation. In the equivalent circuit model, the photocurrent, $I_{PHOTO}$, sees an essentially open circuit in the path to the base of transistor 222 because transistor 222 is "off." Thus, $I_{PHOTO}$ passes through R13 as shown in FIG. 3a. The voltage drop across R13 caused by $I_{PHOTO}$ will be equal to the base-emitter voltage drop across transistor 222 because R13 is coupled between the base and emitter of 222. To turn "on" the transistor 222, the voltage drop across the base and emitter of transistor 222 needs to be about 0.47 V to 0.53 V. By selecting a value of R13 that will keep the voltage drop across R13 below 0.47 V to 0.53 V in response to a photocurrent that corresponds with low intensity incident light, R13 can attenuate the phototransistor's output in response to low intensity incident light. An exemplary value for R13 is 10 MΩ. Because the phototransistor is not turned "on," the photocurrent is kept away from the base, preventing amplification of the photocurrent (the base of the transistor 222 drives the gain of the phototransistor S1). When transistor 222 is turned "on," photocurrent will feed the base of transistor 222, and the output of the phototransistor will be amplified accordingly. Once on line 208, the photocurrent will be further diverted to ground through R6, through the resistor capacitor circuit 248, and through R4 (via C9). The current passing through the resistor capacitor circuit 248 will begin the charging of capacitor C12 at line 205.

As more light reaches the phototransistor, $I_{PHOTO}$ will increase. When $I_{PHOTO}$ is sufficiently large to create a voltage drop across R13 of about 0.47 V to 0.53 V, the transistor 222 will turn "on." Also, if intense incident light, such as light from a welding arc, reaches the phototransistor, a large photocurrent will be produced. The large photocurrent passing through R13 will quickly create a voltage drop across R13 that is sufficient to turn "on" transistor 222, thus achieving a sharp increase in phototransistor output in response to high intensity light. While in the preferred embodiment R13 is a resistor, it is conceivable that any nonreactive element providing a quick voltage drop in response to a current may be used in the invention.

When transistor 222 first activates, the feedback transistor Q2 will still be in the "off" state while it waits for the voltage on line 205 to charge through capacitor C12. FIG. 3b depicts the equivalent circuit model for the sensor circuit in this mode of operation. Part of $I_{PHOTO}$ will be fed into the base of transistor 222 and part of $I_{PHOTO}$ will be diverted through R13. The current fed into the base of 222 will drive the gain for the phototransistor. The output of the phototransistor on line 208 will be the sum of the emitter current of transistor 222 and the current diverted through R13. Once on line 208, the current will be further diverted to ground through R6, through the resistor capacitor circuit 248, and through R4 (via C9).

As previously explained, the current passing through the resistor capacitor circuit 248 will cause the capacitor C12 to charge. As C12 charges, the voltage on line 205 will begin to increase toward 0.6 V. Once the voltage on line 205 reaches about 0.6 V, the feedback transistor Q2 is turned "on." Once Q2 is activated, it drains some of the photocurrent away from the base of the transistor 222 as shown in FIG. 3c. By diverting photocurrent from the base of the phototransistor, the feedback transistor Q2 decreases the gain provided by the phototransistor, thereby causing a drop in the phototransistor output despite an incident light level that remains essentially constant. This biasing operation allows the phototransistor to maintain a constant signal level for a steady light intensity.

The signal on line 208 if fed into an amplifier 210. The signal is first passed through a capacitor C9 to block the DC component of the detected signal. Line 209 contains the DC blocked detected signal. The current on line 209 is diverted to ground via resistor R4.

The sensor circuit operates in the presence of both AC welds and DC welds. In an AC weld (also known as a MIG weld), the welding light is pulsating. Thus, the phototransistor will detect a pulsating light signal. The frequency of the pulsations is often 120 Hz. In a DC weld (also known as a TIG weld), the welding light is substantially continuous, with the exception of a small AC component. When an AC weld is present, the phototransistor will produce a pulsating output on line 208. The variations in the voltage signal due to the pulses will be passed through the capacitor to line 209 and fed into the amplifier. The amplifier will then provide gain for the signal on line 209 which is sufficient to trigger the delivery of a "dark state" drive signal to the shutter assembly 400. The slow charge time of capacitor C14 in selector circuit 316 will prevent the transition from a dark state to a clear state during brief interruptions in the AC weld pulses. Before C14 recharges, the next AC pulse will cause the capacitor to discharge before a "clear state" drive signal is triggered.

When a DC weld is present, the phototransistor will quickly produce an output on line 208 catching the rising edge of the DC weld. This sudden rise in voltage on line 208 will be passed through to the amplifier 210 causing a signal on line 211 sufficient to trigger the delivery of a "dark state" drive signal to the shutter assembly 400. Thereafter, capacitor C9 will block the DC component of the DC weld, allowing only the AC variations in the DC weld to pass through to the amplifier. The amplifier 210 must have a gain sufficient to keep the shutter assembly in the dark state when the AC variations in the DC weld reach the amplifier.

The amplifier 210 is a closed loop, noninverting amplifier as described above. The output of the amplifier is fed into a selector circuit 316. The selector circuit 316 uses a phototransistor to send a selection signal to the delivery circuit 315 via line 107. As previously explained, for the selector circuit 316 to send a signal indicating that a "dark state" drive signal should be delivered to the shutter assembly, a 0.6 V signal needs to be applied to the base of control transistor Q3 on line 211. Thus, it can be seen that amplifier 210 must produce a signal of about 0.6 V on line 211 when the phototransistor produces a signal on line 208 indicative of the presence of a welding arc. The gain of amplifier 210 must therefore be set such that it will sufficiently amplify its input voltage to produce an output voltage of about 0.6 V when the input signal on line 209 indicates the presence of a welding arc. The gain of the amplifier 210 is set by resistors R9 and R3 in the feedback loop. The gain of the amplifier having this configuration is:

$$\text{Gain} = (R9/R3) + 1$$

The inventor herein has noted that a gain of about 3.67 will be sufficient for the amplifier to trigger the "dark state" drive signal when a welding arc is lit. Exemplary values for R9 and R3 would be 1 MΩ and 374 kΩ respectively.

Figure 4:
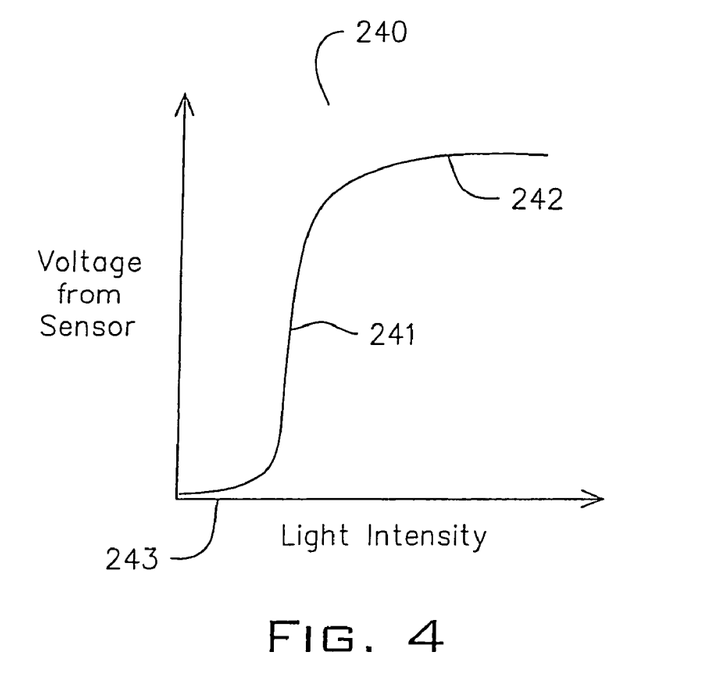
FIG. 4 is a graph depicting the voltage from the phototransistor as a function of incident light intensity.

Referring to FIG. 4, the output of the phototransistor will be described in relation to the amount of incident light. The curve of FIG. 4 depicts the output of the phototransistor on line 208 (on the vertical axis) as a function of the intensity of incident light (on the horizontal axis). The curve has a relatively steep portion 241 for lower intensity incident light and a less steep portion 242 for higher intensity incident light. The operation of the phototransistor in these portions of the curve are discussed in detail in prior U.S. Pat. Nos. 5,248,880 and 5,252,817, the disclosures of which have been incorporated by reference. Of note for the present invention is curve portion 243 which represents an extremely low voltage response from the phototransistor when the incident light has low intensity. This gap in the voltage response of the phototransistor is due to the effect of R13 whereby it prevents the activation of the phototransistor in the presence of low intensity light. However, the invention still provides a sharp increase in phototransistor output when the light intensity increases as can be seen by the steep slope of curve portion 241.

The invention has been disclosed herein in the context of the inventor's preferred embodiment. However, changes and modifications thereto as would be apparent to one of ordinary skill in the art are intended to be included by the inventor and the invention should be limited only by the scope of the claims appended hereto, and their equivalents.

What is claimed is:

1. An auto darkening eye protection device comprising:
    a shutter assembly, the shutter assembly being adjustable to a plurality of shade levels;
    a light sensing circuit for sensing incident light and providing an output indicative of the shade level at which the shutter assembly should be operated, the light sensing circuit comprising:
        a phototransistor operative to receive incident light and produce an output representative thereof; and
        an amplifier coupled to the phototransistor for amplifying the phototransistor output;
    a control circuit configured to receive the amplifier output and provide a drive signal to the shutter assembly responsive to the amplifier output, the drive signal being operative to drive the shutter assembly to one of the plurality of shade levels; and
    a power supply comprising a solar cell coupled to the amplifier such that the amplifier will receive power when incident light powers the solar cell.

2. The auto darkening eye protection device of claim 1 wherein the solar cell is coupled to the phototransistor such that the phototransistor will receive power when incident light powers the solar cell.

3. The auto darkening eye protection device of claim 1 further comprising a secondary power source wherein the solar cell recharges the secondary power source.

4. The auto darkening eye protection device of claim 2 further comprising a secondary power source wherein the solar cell recharges the secondary power source.

5. The auto darkening eye protection device of claim 3 wherein the secondary power source will supplement power supplied by the solar cell to provide power to a circuit component, wherein the solar cell provides power solely to another circuit component with such power not being supplemented by the secondary power source.

6. The auto darkening eye protection device of claim 1 wherein the amplifier comprises a closed loop non-inverting amplifier.

7. The auto darkening eye protection device of claim 1 wherein the amplifier provides a gain to the output of the light sensing circuit sufficient to trigger the control circuit to drive the shutter assembly to a dark shade level when the phototransistor receives a light input having an intensity indicative of a welding arc being present.

8. The auto darkening eye protection device of claim 1 further comprising a non-reactive element coupled between the base and emitter of the phototransistor when the light received by the phototransistor has a low intensity.

9. The auto darkening eye protection device of claim 1 wherein the light sensing circuit further comprises a capacitor in circuit between the phototransistor and the amplifier for blocking DC in the phototransistor output.

10. The auto darkening eye protection device of claim 1 wherein the phototransistor is a planar phototransistor.

11. The auto darkening eye protection device of claim 10 wherein the phototransistor is configured for a surface mount.

12. An auto darkening eye protection device comprising:
    a shutter assembly, the shutter assembly being adjustable to a plurality of shade levels;
    a light sensing circuit for sensing incident light and providing an output indicative of the shade level at which the shutter assembly should be operated, the light sensing circuit comprising:
        a phototransistor operative to receive incident light and produce an output representative thereof; and
        an amplifier coupled to the phototransistor for amplifying the phototransistor output;
    a control circuit configured to receive the amplifier output and provide a drive signal to the shutter assembly responsive to the amplifier output, the drive signal being operative to drive the shutter assembly to one of the plurality of shade levels; and
    a power supply comprising a solar cell coupled to the phototransistor and the amplifier such that the phototransistor and the amplifier will receive power when incident light powers the solar cell.

13. The auto darkening eye protection device of claim 12 further comprising a secondary power source wherein the solar cell recharges the secondary power source.

14. The auto darkening eye protection device of claim 12 wherein the secondary power source will supplement power supplied by the solar cell to provide power to a circuit component, wherein the solar cell provides power solely to another circuit component with such power not being supplemented by the secondary power source.

15. The auto darkening eye protection device of claim 12 wherein the amplifier comprises a closed loop non-inverting amplifier.

16. The auto darkening eye protection device of claim 12 wherein the amplifier provides a gain to the output of the light sensing circuit sufficient to trigger the control circuit to drive the shutter assembly to a dark shade level when the phototransistor receives a light input having an intensity indicative of a welding arc being present.

17. The auto darkening eye protection device of claim 12 further comprising a non-reactive element coupled between the base and emitter of the phototransistor when the light received by the phototransistor has a low intensity.

18. The auto darkening eye protection device of claim 12 wherein the light sensing circuit further comprises a capacitor in circuit between the phototransistor and the amplifier for blocking DC in the phototransistor output.

19. An auto darkening eye protection device comprising:
a shutter assembly, the shutter assembly being adjustable to a plurality of shade levels;
　a light sensing circuit for sensing incident light and providing an output indicative of the shade level at which the shutter assembly should be operated, the light sensing circuit comprising:
　　a phototransistor operative to receive incident light and produce an output representative thereof; and
　　an amplifier coupled to the phototransistor for amplifying the phototransistor output;
a control circuit comprising
　a signal generator for generating a voltage level and a frequency signal to the shutter assembly, the voltage level and frequency signal being operative to drive the shutter assembly to one of the plurality of shade levels; and
　an activation circuit for activating the signal generator, the activation circuit responsive to the amplifier output; and
　a power supply comprising a solar cell coupled to the light sensing circuit and control circuit for powering same, the solar cell being coupled to the amplifier and activation circuit such that the amplifier and activation circuit will receive power when incident light powers the solar cell.

* * * * *